United States Patent [19]

Sreekrishna et al.

[11] Patent Number: 4,857,467
[45] Date of Patent: Aug. 15, 1989

[54] CARBON AND ENERGY SOURCE MARKERS FOR TRANSFORMATION OF STRAINS OF THE GENES PICHIA

[75] Inventors: Kotikanyadan Sreekrishna; Motohiro Fuke, both of Bartlesville, Okla.

[73] Assignee: Phillips Petroleum Company, Bartlesville, Okla.

[21] Appl. No.: 887,300

[22] Filed: Jul. 23, 1986

[51] Int. Cl.[4] .................. C12N 1/16; C12N 15/00; C12N 5/00
[52] U.S. Cl. ..................... 435/255; 435/938; 435/172.2; 435/172.3; 435/240.26; 935/66; 935/69; 935/97
[58] Field of Search ............... 435/254, 255, 938, 911, 435/921, 940, 944, 34; 935/69, 66, 97

[56] References Cited

U.S. PATENT DOCUMENTS 4,617,274  10/1986  Wegner ........................ 435/255

FOREIGN PATENT DOCUMENTS 2125047  2/1984  United Kingdom .

OTHER PUBLICATIONS

Cregg et al., Mol. and Cell. Biol., vol. 5, 1985, pp. 3376–3385.
Proc. Natl. Acad. Sci. USA, Kevin Struhl, et al., vol. 76, No. 3, pp. 1035–1039 3/79, High-Frequency Transformation of Yeast: Autonomous Replication of Hybrid DNA Molecules.
Proc. Natl. Acad. Sci. USA, Chu-Lai Hsiao et al., vol. 76, No. 8, pp. 3829–3833, 8/79, High-Frequency Transformation of Yeast by Plasmids Containing the ARG4 Gene.
Proc. Natl. Acad. Sci. USA, Dan T. Stinchcomb et al., vol. 77, No. 8, pp. 4559–4563, Eukaryotic DNA Segments Capable of Autonomous Replication in Yeast.
Proc. Natl. Acad. Sci. USA, Clarence S. M. Chan et al., vol. 77, No. 11, pp. 6329–6333, Automatically Replicating Sequences in *Saccharomyces cerevisiae*.
Proc. Natl. Acad. Sci. USA, Terry L. Orr-Weaver et al., vol. 78, No. 10, pp. 6354–6358, 10/81, Yeast Transformation: A Model System for the Study of Recombination.
Cell, Marian Carlson et al., vol. 28, 145–154, 1/82, Two Differentially Regulated mRNAs with Different 5' Ends Encode Secreted and Intracellular Forms of Yeast Invertase.
Gene, Thomas D. Webster and Robert C. Dickson, vol. 26 (1983) pp. 243–252, Direct Selection of *Saccharomyces cerevisiae* Resistant to the Antibiotic G418 Following Transformation with a DNA Vector Carrying the Kanamycin-Resistance Gene of Tn903.
Gene, K. Sreekrishna et al., vol. 28 (1984), pp. 73–81, Transformation of Kluyveromyces Lactis with the Kanamycin (G418) Resistance Gene of Tn903.

*Primary Examiner*—Elizabeth C. Weimar
*Assistant Examiner*—P. Carson
*Attorney, Agent, or Firm*—J. E. Phillips

[57] ABSTRACT

Yeast strains are transformed with, and selected for, using DNA fragments encoding a gene function not present in the wild-type yeast strains. The invention requires transforming the yeast with DNA fragments which comprise the gene function which the wild-type yeast strain is lacking; regeneration of the transformants on a non-selective regeneration medium; then selection of those colonies which are capable of growth on a carbon and energy source which requires expression of the gene function provided by the DNA fragment. Thus, transformation with such DNA fragments allows for positive selection of transformed strains.

3 Claims, 1 Drawing Sheet

CARBON AND ENERGY SOURCE MARKERS FOR TRANSFORMATION OF STRAINS OF THE GENES PICHIA

This invention relates to the field of recombinant DNA technology. In one of its aspects, the invention relates to the transformation of prototrophic yeast strains. In another aspect, the invention relates to dominant transformation markers useful for the transformation of yeast strains of the genus Pichia.

BACKGROUND

Commercial efforts employing recombinant DNA technology for producing various polypeptides have, up to now, centered predominantly on *Escherichia coli* as a host organism. However, in some situations *E. coli* may prove to be unsuitable as a host. For example, *E. coli* contains a number of toxic pyrogenic factors that must be eliminated from any polypeptide useful as a pharmaceutical product. The efficiency with which this purification can be achieved will, of course, vary with the particular polypeptide. In addition, the polyteolytic activities of *E. coli* can seriously limit yields of some useful products. Moreover, proteins expressed at high levels in *E. coli* are packaged into refractory bodies and are difficult to solubilize. Thus recovery of active proteins from *E. coli* can frequently be troublesome. These and other considerations have led to increased interest in alternative hosts, in particular, the use of eukaryotic organisms for the production of polypeptide products is appealing.

The availability of means for the production of polypeptide products in eukaryotic systems, e.g., yeast, could provide significant advantages relative to the use of prokaryotic systems such as *E. coli* for the production of polypeptides encoded by recombinant DNA. Yeast has been employed in large scale frementations for centuries, as compared to the relatively recent advent of large scale *E. coli* fermentations. Yeast can generally be grown to higher cell densities than bacteria and are readily adaptable to continuous fermentation processing. In fact, growth of yeast such as *Pichia pastoris* to ultra-high cell densities, i.e., cell densities in excess of 100 g/L, is disclosed by Wegner in U.S. 4,414,329 (assigned to Phillips Petroleum Co.). Additional advantages of yeast hosts include the fact that many critical functions of the organism, e.g., oxidative phosphorylation, are located within organelles, and hence are not exposed to the possible deleterious effects of the organism's production of polypeptides foreign to the wild-type host cells. As a eukaryotic organism, yeast may prove capable of glycosylating expressed polypeptide products where such glycosylation is important to the bioactivity of the polypeptide product. It is also possible that as a eukaryotic organism, yeast will exhibit the same codon preferences as higher organisms, thus tending toward more efficient production of expression products from mammalian genes or from complementary DNA (cDNA) obtained by reverse transcription from, for example, mammalian mRNA.

The development of poorly characterized yeast species as host-vector systems is severely hampered by the lack of strains having auxotrophic mutations. Such mutant strains are often not available, precluding a direct selection for transformants by auxotrophic complementation. In order to avoid the need for auxotrophic mutants, it would be desirable to have available positive selection markers which would allow direct transformation of wild-type hosts. Wild-type hosts are desirable host organisms because they are readily available and require no strain manipulation in order to be useful as hosts to inserted DNA. Thus, dominant transformation markers which allow the direct transformation of prototrophic hosts are desirable.

OBJECTS OF THE INVENTION

An object of the present invention, therefore, is the development of dominant selection markers for use in the transformation of yeast strains.

Another object of the present invention is the development of methods for selection of yeast strains which have been transformed with positive selection markers.

These and other objects of the invention will become apparent from inspection of the disclosure, drawing and claims herein provided.

STATEMENT OF THE INVENTION

In accordance with the present invention, there have been developed positive selection methods for transforming yeast strains which comprises transforming the yeast with a DNA fragment comprising at least one gene function in which prototrophic yeast strains are deficient or lacking, as well as additional, optional DNA which one wishes to have expressed in the host, but which does not provide any selectible phenotype to the transformed host; regenerating the transformants on a non-selective regeneration medium; and selecting those regenerated colonies which are capable of growth on a carbon and energy source which requires expression of the gene function provided by said DNA fragment.

This aspect of the invention provides methodology useful for the replacement of normal chromosomal genes with in vitro generated mutant alleles for examining gene structure and function, since this technique requires a selectable vector-borne marker that does not contain sequences of homology to the host chromosome, and the DNA fragment encoding the gene function which the host lacks would have no homology with the host.

This aspect of the invention also provides a means to introduce dominant markers into hosts for genetic mapping experiments, especially useful for DNA segments which have no recognizable phenotypes.

This aspect of the invention also allows one to screen very large numbers of cells on a single plate for the incidence of integrative transformation of the DNA fragment which encodes the gene function which the wild-type host lacks, since there is no chance for reversion by the transformants as there is when a phenotypic markers are introduced by mutation of native DNA sequences.

DETAILED DESCRIPTION OF THE INVENTION

Figure 1:
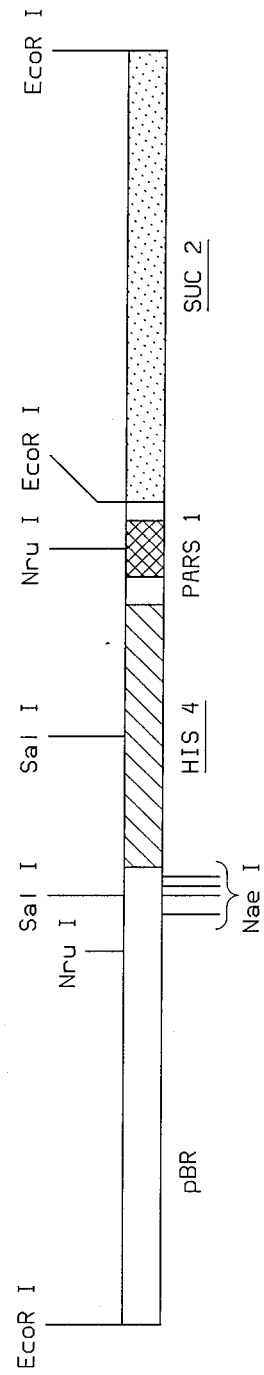
FIG. 1 is a linearized restriction map of the closed circular plasmid pTSU1.

In accordance with the present invention, a method for the transformation of yeast strains is provided by transforming said yeast with a DNA fragment which encodes a gene function in which prototrophic strains of the yeast are deficient or lacking; regenerating the transformants on a non-selective regeneration medium;

and selecting those regenerated colonies which are capable of growth on a carbon and energy source which requires expression of the gene function provided by said DNA fragment. Incorporation of such gene fragments allows for growth of the transformed strain on a carbon and energy source which wild-type yeast strains would otherwise be unable to employ as carbon and energy source. Thus, transformants of prototrophic yeast strains can be identified by their ability to grow on carbon and energy sources on which wild-type strains of such yeast strains are unable to grow.

The host yeast cells employed in the practice of the present invention can be either prototrophic or auxotrophic strains. The advantage of utilizing prototrophic strains is that they are readily available, and frequently have better growth properties than do auxotrophic strains. On the other hand, auxotrophic strains allow for selection of transformants and continued application of selective pressure on the transformants by complementation of the missing gene function.

Exemplary genera of yeast contemplated to be useful in the practice of the present invention are Pichia, Saccharomyces, Kluyveromyces, Candida, Torulopsis, Hansenula, Schizosaccharomyces, Citeromyces, Pachysolen, Debaromyces, Metschunikowia, Rhodosporidium, Leucosporidium, Botryoascus, Sporidiobolus, Endomycopsis, and the like. Preferred genera are those selected from the group consisting of Pichia, Saccharomyces, Kluyveromyces and Hansenula, because the ability to manipulate the DNA of these yeast strains has, at present, been more highly developed than for the other genera mentioned above.

Exemplary strains of Pichia contemplated within the scope of the present invention are the prototrophic strains *Pichia pastoris* NRRL Y-11430, and *Pichia pastoris* NRRL Y-11431; the histidine requiring strain *Pichia pastoris* NRRL Y-15851; the arginine requiring strain *Pichia pastoris* NRRL Y-18014; the histidine/arginine requiring strain *Pichia pastoris* NRRL Y-18017, and the like.

The gene functions in which some strains of the genus Pichia are deficient include those involved in the utilization of such carbon and energy sources as sucrose (i.e., the invertase gene), melibiose (i.e., the α-galactosidase gene), lactose (i.e., the β-galactosidase and lactose permease genes), maltose (i.e., the β-glucosidase gene) and the like.

Exemplary strains of Saccharomyces contemplated within the scope of the present invention are *Saccharomyces cerevisiae*, *Saccharomyces italicus*, *Saccharomyces rouxii*, and the like.

The gene function in which some strains of Saccharomcyes is deficient is the ability to utilize lactose as carbon and energy source.

Exemplary strains of Kluyveromyces contemplated within the scope of the present invention are *Kluyveromyces fragilis*, *Kluyveromyces lactis*, and the like.

The gene function in which some strains of Kluyveromyces is deficient is the ability to utilize melibiose as carbon and energy source.

Exemplary strains of Hansenula contemplated within the scope of the present invention are *Hansenula polymorpha*, *Hansenula anomala*, *Hansenula capsulata*, and the like.

The gene function in which some strains of Hansenula is deficient is the ability to utilize lactose as carbon and energy source.

It is expected that all yeast strains can be transformed in accordance with the present invention by:
 (a) digestion of the cell walls to produce spheroplasts;
 (b) mixing the spheroplasts with transforming DNA (derived from a variety of sources and containing both native and non-native DNA sequences);
 (c) regenerating the transformed cells.

The regenerated cells are then screened for the incorporation of the transforming DNA.

It has been demonstrated that yeast strains of the genera Pichia, Saccharomyces, Kluyveromyces, and Hansenula, can be transformed by enzymatic digestion of the cell walls to give spheroplasts; the spheroplasts are then mixed with the transforming DNA and incubated in the presence of calcium ions and polyethylene glycol, then transformed spheroplasts are regenerated in rich regeneration medium (see Examples for an exemplary recipe). The transforming DNA includes the functional gene in which the host strain is deficient, thus only transformed cells will survive upon subsequent growth on selective growth medium.

For example, to prepare Pichia spheroplasts, the cells are first contacted with a sulfhydryl group reducing agent, such as, for example, dithiothreitol or β-mercaptoethanol. An example of a specific solution containing a sulfhydryl group reducing agent is the dithiothreitol in SED buffer described in the Examples. Enzymatic digestion of the cell walls can then be accomplished by contacting the strain to be transformed with any of the many cell wall degrading reagents known to those of skill in the art, such as for example Zymolyase (Miles Laboratories), Glusulase (Endo Laboratories), and the like. Although a wide variety of temperatures, contact times and dosage levels are operable, generally, when using, for example, Zymolyase 100,000 (100,000 units/g) about 10 μg to 100 μg of cell wall degrading reagent per 10 mL of cell suspension are employed for spheroplast formulation. Preferably about 20–30 μg of Zymolyase 100,000 per 10 mL of cell suspension is employed. Temperature is generally maintained at about 25° C. or above, but less than about 35° C. Preferably, temperature is maintained at about 30° C. Contact time is generally at least about 5 minutes and usually no greater than about 15 minutes. Preferably, contact time in the range of about 5–10 minutes is employed. While many buffered media are suitable, it is essential that cells to be converted to spheroplasts be suspended in a buffer which is iso-osmotic with the cells, such as, for example, SCE buffer (sorbitol/citrate/EDTA; see Examples for recipe).

The spheroplasts can be transformed by contact with virtually any amount of recombinant DNA material. Generally, at least about 5 μg of transforming DNA per 100 μL of spheroplast containing solution (containing between about $1-3 \times 10^7$ spheroplasts per 100 μL) are employed. Where only small amounts of recombinant DNA material are available, sonicated *E. coli* DNA can be used to supplement the amount of available DNA, thereby improving transformation frequencies by minimizing the handling losses of recombinant DNA material during experimental manipulation.

Transformed spheroplasts are then treated under cell wall regenerating conditions. Cell wall regenerating conditions comprise adding a sample containing transformed spheroplasts to melted regeneration agar maintained at about 40°–60° C. A typical regeneration agar provides a balanced osmotic media and comprises:

| | |
|---|---|
| sorbitol (or KCl) | about 1 M (0.6 M) |
| dextrose | about 1.0 M |
| yeast nitrogen base | about 13.4 g/L |
| Bacto-agar | about 1% |

The transformed spheroplasts in melted regeneration agar are poured over a bottom layer of regeneration agar and then incubated at about 25°–35° C. for about 3–10 days.

Transformants which have incorporated a functional copy of the gene function which the un-modified host lacked are screened employing the following two-step procedure:
(1) the transformed spheroplasts are allowed to regenerate under non-selective regeneration conditions, then
(2) the regenerants produced in accordance with the preceding step are plated on selective growth media, and those colonies which survive under selection pressure are identified for further evaluation.

As an example, Suc+ transformants of *P. pastoris* were obtained by using the above-described two step procedure. In the first step, the Pichia spheroplasts transformed with SUC2 were allowed to regenerate on a nonselective regeneration medium. In the second step, the regenerated cells were plated on sucrose plates to screen for Suc+ colonies. The first step, i.e. the regeneration step, aids the recovery by the spheroplasts from the rigors of the spheroplasting procedure. Once the cells have been regenerated, the gene(s) required for growth on a "foreign" carbon and energy source are more readily expressed by the transformed organism. Screening for transformants was then conducted several days after regeneration of the spheroplasts.

When the gene function necessary for growth of a yeast strain on a foreign, i.e. not usually utilized, carbon and energy source is carried on an autonomous vector, there are certain non-foreign carbon source utilizers which sometimes will continue to grow on the foreign carbon source due to cross-feeding. Non-foreign carbon source utilizers arise among the segregants where the autonomous plamid is not passed on to all daughter cells upon cell division. Cross-feeding occurs when the gene function required for growth on the foreign carbon source is provided by secretion of active enzyme by the cells which retain plasmid. Thus, the observation of cross-feeding is an indication that the enzyme(s) required for growth on the foreign carbon and energy source are secreted by the cells which retain the autonomous plasmid.

In contrast, when the gene function required for growth of a yeast strain on a foreign carbon and energy source is incorporated into the genome of the host by integrative transformation, the problem of non-foreign carbon source utilizing segregants contaminating the positive transformants is avoided, because each new generation of cells receives a copy of all the parental DNA. Thus, the random segregation of plasmid DNA into each succeeding generation of cells is eliminated by supplying the required DNA by integrative transformation.

The present invention will now be described in greater detail with reference to the following non-limiting examples.

EXAMPLES

The following reagents and media are used throughout the following examples:

| | |
|---|---|
| SED | 2 M Sorbitol<br>0.2 M EDTA<br>1 M DTT<br>-- adjust to pH 8 |
| SCE | 2 M Sorbitol<br>1 M Sodium utrate<br>2 M EDTA<br>-- adjust to pH 5.8 with HCl. |
| CaS | 1 M Sorbitol<br>1 M Tris-HCl (pH 7.5)<br>1 M CaCl$_2$ |
| TE-buffer | 50 mM Tris-HCl, pH 7.5<br>1 mM EDTA |
| PEG Solution | 2 g. PEG 4000<br>-- bring total volume<br>to 10 mL. with H$_2$O |
| SOS | 1 M Sorbitol<br>0.3 X YPD medium<br>10 mM CaCl$_2$ |
| Complex Media (per liter) | |
| YPD: | Yeast extract (10 g), peptone (20 g), and dextrose (10 g.) |
| LB: | Yeast extract (5 g), tryptone (10 g), NaCl (10 g), and adjusted to pH 7.5 with 5 N NaOH. |
| LBAp: | LB + 50 mg ampicillin. |
| For plates, 15 g agar was added. | |
| Yeast Minimal Media (per liter) | |
| MD: | Yeast nitrogen base without amino acids (YNB, 13.4 g), dextrose (10 g), and biotin (400 μg). |
| MSu: | YNB (13.4 g), sucrose (10 g), and biotin (400 μg). |
| MDH: | MD + histidine (40 mg). |
| MSuH: | Msu + histidine (40 mg). |
| For plates, 15 g Noble Agar was added. | |
| Regeneration Media (per liter) | |
| SD (R): | YNB (13.4 g), Noble Agar (10 g), biotin (400 μg), AA mix (950 mg - 50 mg each of all the common amino acids, except histidine), and Sorbitol (180 g). |
| SDH (R): | SD (R) + histidine (40 mg). |
| KD (R): | YNB (13.4 g), Noble Agar (10 g), biotin (400 μg), AA mix (950 mg), and KCl (0.6 M 44.7 g). |
| KDH (R): | KD (R) + histidine (40 mg). |
| KSuH (R): | Same as KDH (R), except that 10 g sucrose is used in the place of 10 g dextrose. |

The sugars, amino acids, antibiotics and biotin were sterilized by membrane filtration.

Fermentation Media (mg% is the number of milligrams of a given component per 100 mL of total media.)

All strains were maintained on MM minimal medium: (KH$_2$PO$_4$, 87.5 mg%; K$_2$HPO$_4$, 12.5 mg%; (NH$_4$)$_2$SO$_4$, 100 mg%; MgSO$_4$·7H$_2$O, 50 mg%, NaCl, 10 mg%; CaCl$_2$·H$_2$O, 10 mg%; FeCl$_3$·6H$_2$O, 5 ng%; ZnSO$_4$·7H$_2$O, 7 ng%; H$_3$BO$_4$, 1 ng%; CuSO$_4$·5H$_2$O, 1 ng%; KI, 1 ng%), pH 5.8 supplemented with 1% glucose or 1% sucrose, 5 ng% biotin, and 2 mg% histidine, as required.

Chemostat cultures were started in two liters of 1× FM -21 minimal medium: (85% H$_3$PO$_4$, 3.5 mL/100 mL; CaSO$_4$·2H$_2$O, 15 mg%; K$_2$SO$_4$, 238 mg%; MgSO$_4$·7H$_2$O, 195 mg%; KOH, 65 mg%; FeSO$_4$·7H$_2$O, 6.5 ng%; CuSO$_4$·5H$_2$O, 6 mg%; ZnSO$_4$·7H$_2$O, 20 mg%; MnSO$_4$·H$_2$O, 3 mg%; biotin, 4.1 ng%; DOW Corning FG-10 antifoam, 8 drops/liter supplemented with 2% glucose or sucrose as required and brought to and maintained at pH 4.0 with NH$_3$ gas.

EXAMPLE I

*Pichia pastoris* Transformation Procedure

A. Cell Growth

1. Inoculate a colony of *Pichia pastoris* GTS115 (NRRL Y-15851) into about 10 mL of YPD medium and shake culture at 30° C. for 12-20 hours.

2. After about 12-20 hours, dilute cells to an $OD_{600}$ of about 0.01-0.1 and maintain cells in log growth phase in YPD medium at 30° C. for about 6-8 hours.

3. After about 6-8 hours, inoculate 100 mL of YPD medium with 0.5 mL of the seed culture at $OD_{600}$ of about 0.1 (or equivalent amount). Shake at 30° C. for about 12-20 hours.

4. Harvest culture when $OD_{600}$ is about 0.2-0.3 (after approximately 16-20 hours) by centrifugation at 1500 g for 5 minutes.

B. Preparation of Spheroplasts

1. Wash cells once in 10 mL of sterile water. (All centrifugations for steps 1-5 are at 1500 g for 5 minutes.)

2. Wash cells once in 10 mL of freshly prepared SED buffer.

3. Wash cells twice in 10 mL of sterile 1M Sorbitol.

4. Resuspend cells in 10 mL SCE buffer.

5. Add 5-10 μL of 3 mg/mL Zymolyase 100,000 (Miles Laboratories). Incubate cells at 30° C. for about 5-10 minutes.

Since the preparation of spheroplasts is a critical step in the transformation procedure, one should monitor spheroplast formation as follows: add 100 μL aliquots of cells to 900 μL of 5% sodium dodecylsulfate (SDS) and 900 μL of 1M Sorbitol before or just after the addition of Zymolyase and at various times during the incubation period. Stop the incubation at the point where cells lyse in SDS but not in Sorbitol.

6. Wash spheroplasts twice in 10 mL of sterile 1M Sorbitol by centrifugation at 1000 g for 5-10 minutes. (The time and speed for centrifugation may vary; centrifuge enough to pellet spheroplasts but not so much that they rupture from the force.)

7. Wash cells once in 10 mL of sterile CaS buffer.

8. Resuspend cells in total of 0.6 mL of CaS buffer.

C. Transformation

1. Add DNA samples (up to 20 μL volume) to 12×75 mm sterile polypropylene tubes. (DNA should be in water or TE buffer; for maximum transformation frequencies with small amounts of DNA, it is advisable to add about 1 μL of 5 mg/mL sonicated *E. coli* DNA to each sample.)

2. Add 100 μL of spheroplasts to each DNA sample and incubate at room temperature for about 20 minutes.

3. Add 1 mL of PEG solution to each sample and incubate at room temperature for about 15 minutes.

4. Centrifuge samples at 1000 g for 5-10 minutes and decant PEG solution.

5. Resuspend samples in 150 μL of SOS solution and incubate for 30 minutes at room temperature.

6. Add 850 μL of sterile 1M Sorbitol and plate aliquots of samples as described below.

D. Regeneration of Spheroplasts

1. Regeneraton Agar Medium: SD(R), SDH(R), KD(R), KDH(R) and KSuH(R) as described above were employed.

2. Plating of Transformation Samples:

Pour bottom agar layer of 10 mL Regeneration Agar per plate at least 30 minutes before transformation samples are ready. Distribute 10 mL aliquots of Regeneration Agar to tubes in a 45° C. bath during the period that transformation samples are in SOS solution. Add aliquots of transformation samples described above to tubes with Regeneration Agar and pour onto bottom agar layer of plates. Add a quantity of each sample to 10 mL aliquots of melted Regeneration Agar held at 45° C. and pour each onto plates containing a solid 10 mL bottom agar layer of Regeneration Agar.

3. Determination of Quality of Spheroplast Preparation:

Remove 100 μL of one sample and spread on YPD agar medium to determine the concentration of unspheroplasted whole cells remaining in the preparation. Add another 100 μL to 10 mL of Regeneration Agar supplemented with 40 μg/mL histidine (KDH(R) or SDH(R)) and plate on KDH or SDH plates to determine total regeneratable spheroplasts. Good values for a transformation experiment are $2\times10^5 - 2\times10^6$ total regeneratable spheroplasts/mL and about $1-2\times10^4$ whole cells/mL.

4. Incubate plates at 30° C. for 3-5 days.

EXAMPLE II

Transformation of *Pichia pastoris* and Screening of Sucrose+ (Suc+) Transformants Pichia strains GTS115 (NRRL Y-15851) and NRRL Y-11430 were transformed according to the procedure of Example I. The transformed spheroplasts were allowed to regenerate on either 0.6M KCl or 1M Sorbitol containing regeneration media. For screening Suc+ colonies, the regenerated cells embedded in agar were carefully dislodged into a sterile 50 mL disposable centrifuge tube, mixed with 10 ml water, and vortexed to disperse the cells from agar. The agar-cells suspension was passed through several folds of sterilized cheesecloth. The agar chunks retained on the cheesecloth were rinsed two times with 10 mL water to recover cells trapped in agar and cloth. The filtrate containing cells and fine agar particles was centrifuged at 5000 rpm in HS-4 rotor for five minutes at room temperature. Under these conditions, cells formed a tight pellet, while agar particles formed a loose pellet on the top of cells. The agar layer was removed by disturbing the tubes gently and pouring off the milky supernatant solution. The tight cell pellet remaining in the tube was suspended in 5 mL water and aliquots were plated on MSu to screen for Suc+ transformants.

Colony Counting

For counting large numbers (>5000) of colonies on a plate, Nikon Type 102 optical microscope was used. Colonies on a small section of the plate were counted under the microscope at 4× magnification (or sometimes 2× magnification, depending on the density of colonies) and the total number of colonies was calculated by multiplying the number of colonies counted within a given area with the total area of the plate. Up to 500,000 colonies on a plate could be easily counted by this method.

Transformation of *Pichia pastoris* with the SUC2 (invertase) Gene

Pichia strain NRRL Y-11430 was transformed with pTSU1 in accordance with the procedure of Example I. Plasmid pTSU1 contains the *S. cerevisiae* invertase gene, Pichia autonomous replication sequence (PARS1) and the Pichia HIS4 gene, as shown by the linearized restriction map set forth in FIG. 1. In order to ensure access to this plasmid by the public upon issuance of this application as a patent, the plasmid pTSU1 in an *E. coli* host has been deposited with the Northern Regional Research Center of the United States Department of Agriculture in Peoria, Ill. This strain has the laboratory designation HB101/pTSU1 and has been assigned accession number NRRL B-18083. For comparison, GTS115 (a histidine requiring strain) was also transformed with the same vector in accordance with the procedure of Example I. As seen in Table I, the total number of NRRL Y-11430 spheroplasts regenerated on Sorbitol regeneration medium [SDH(R)] is fivefold higher than the corresponding number for the strain NRRL Y-15851(GTS115).

TABLE I

Regeneration of *Pichia pastoris* Spheroplasts*

| Strain, NRRL Y- | Number of Colonies (as a function of medium employed) | | |
|---|---|---|---|
|  | YPD | SDH (R) | KDH (R) |
| 15851 (GTS115) | 2450 | 16,000 | 21,000 |
| 11430 | 1700 | 80,000 | 500,000 |

*Following transformation of Pichia spheroplasts, aliquots were plated on SDH (R) or KDH (R) to determine the number of viable spheroplasts (i.e., regenerable spheroplasts). An aliquot was also plated on YPD, on which only intact cells can grow. Thus, the number of colonies on YPD reflects the number of intact cells, i.e., those cells which have not been spheroplasted during zymolyase treatment.

A further enhancement in the regeneration of NRRL Y-11430 was seen when 0.6M KCl is used in the place of 1M Sorbitol as osmotic stabilizer in the regeneration medium. When Pichia transformants were plated on sucrose containing regeneration media [KSuH(R)] to select for Suc+ transformants, a large number of colonies appeared in both transformed and control plates. It was later found that the amino acid (AA) mix present in the regeneration medium serves as carbon source to such an extent that it made direct selection for Suc+ Pichia transformants not feasible. The AA mix could not be omitted from the regeneration medium because it was essential for spheroplast regeneration. To screen for Suc+ transformants, the regenerated cells were therefore pooled and aliquots were placed on MSu plates. The results are given in Table II.

TABLE II

Suc+ Transformants Obtained by Plating Aliquots of a Pool of Regenerated Pichia Cells Transformed with pTSU1*

| Source of Cells | No. of Cells Plated | No. of Colonies Suc+ | His+ | Ratio Total Suc+ |
|---|---|---|---|---|
| NRRL Y- |  |  |  |  |
| 11430 Pool | $1.8 \times 10^7$ | 0 | NA** | — |
| (control) | $7.2 \times 10^7$ | 0 | NA | — |
|  | $1.4 \times 10^7$ | 0 | NA | — |
| 11430 Pool | $5 \times 10^7$ | 600 | NA | $8.3 \times 10^4$ |
| (transformed with pTSU1) | $2 \times 10^8$ | 2400 | NA | $8.3 \times 10^4$ |
| 15851 (GTS115) Pool | $2 \times 10^7$ | 0 | 0 | — |
| (control) | $10^8$ | 0 | 0 | — |
| 15851 (GTS115) Pool | $3 \times 10^6$ | 400 | 470 | $7.5 \times 10^3$ |
| (transformed with pTSU1) | $1.1 \times 10^7$ | 1100 | 1360 | $1 \times 10^4$ |
|  | $2.2 \times 10^7$ | 3200 | 3000 | $7 \times 10^3$ |

*Pichia strains GTS115 and 11430 were transformed with pTSU1 and the transformed spheroplasts were allowed to regenerate on regeneration plates SDH (R) or KDH (R). The regenerated cells were pooled (as described in the first paragraph of Example II) and plated on MSu to determine the number of Suc+ colonies. When applicable, regenerated cells were also plated on MD to determine the number of His+ colonies. The number of cells plated was determined by plating appropriately diluted cells on complete medium (MDH for GTS115 and MD for 11430) on which all cells should grow.
**NA = not applicable Suc+ colonies were observed at a frequency of 1 per $8 \times 10^4$ cells for NRRL Y-11430 and 1 per $10^4$ cells for NRRL Y-15851 (GTS115). As expected, with the corresponding untransformed Pichia, Suc+ colonies were never seen. In the case of GTS115 (a histidine auxotroph), there was a good correlation between the number of Suc+ and His+ colonies suggesting that the two markers are retained at about the same frequency. Because NRRL Y-11430 is a prototrophic strain, this kind of correlation could not be directly verified with this strain.

Stability of Suc+ GTS115 Transformants

The plasmid pTSU1 contains the DNA fragments necessary to allow it to replicate autonomously in Pichia cells. Such a plasmid can be lost during cell division as there are no rigorous control mechanisms to ensure the distribution of plasmid into every progeny cell. The stability of a plasmid in a transformant is an important parameter in evaluating the usefulness of a recombinant yeast. The plasmid stability can be easily determined by estimating the percent of cells that retain the plasmid-borne markers; in this case, Suc+ for NRRL Y-11430 and both Suc+ and His+ for NRRL Y-15851 (GTS115). In the case of GTS115/pTSU1 transformants (four independent transformants were tested), the plasmid stability was identical under selection pressure for either SUC2 or HIS4 function, suggesting that expression of SUC2 gene in Pichia does not have any deleterious effects on the host cell. This was further confirmed by comparing the stability of a HIS4 plasmid (pYJ30 which contains the Pichia HIS4 gene, the Pichia autonomous replication sequence PARS1 and pBR322 sequences; see FIG. 1) with HIS4 SUC2 plasmid (pTSU1) in GTS115. If the SUC2 gene has any deleterious effect, then pTSU1 should be retained at a drastically reduced frequency compared to the retention of pYJ30. As seen in Table III, there is no significant difference between the stability of pYJ30 and pTSU1 in GTS115.

TABLE III

Stability of Plasmid-borne Marker(s) in GTS115/pYJ30 and GTS115/pTSU1 Transformants*

| Transformant | Plasmid Size Kb | Number of Colonies (medium employed) | | | Marker Stability % | |
|---|---|---|---|---|---|---|
|  |  | (MDH) | (MD) | (MSu) | His+ | Suc+ |
| GTS115/pYJ30-1 | 7.1 | 152 | 10 | NA** | 6.6 | NA |
| GTS115/pYJ30-2 | 7.1 | 500 | 101 | NA | 20.0 | NA |
| GTS115/pYJ30-3 | 7.1 | 120 | 29 | NA | 24.0 | NA |
| GTS115/pYJ30-4 | 7.1 | 205 | 61 | NA | 29.0 | NA |
| GTS115/pTSU1-1 | 12.5 | 143 | 3 | 4 | 2.0 | 2.8 |
| GTS115/pTSU1-2 | 12.5 | 182 | 11 | 11 | 6.0 | 6.0 |
| GTS115/pTSU1-3 | 12.5 | 800 | 300 | 300 | 37.5 | 37.5 |
| GTS115/pTSU1-4 | 12.5 | 255 | 14 | 12 | 5.5 | 4.7 |

*To determine the stability of the markers in GTS115, transformants were grown for 5–6 generations in MD (i.e., under selection pressure for His+ marker.) Aliquots were then plated on MDH to determine the total number of cells plated and on MD and MSu(when applicable) to determine the percent cells retaining the His+ and Suc+ (when applicable) markers.
**NA = not applicable Stability of Suc+ 11430 Transformants With Suc+ NRRL Y-11430 transformants, slightly different results compared to that with Suc+ GTS115 were obtained. The stability of the Suc+ marker in the presence of selection pressure for SUC2 gene function was only 0.1% compared to more than 1% with GTS115 transformants. In the absence of any selection pressure, the Suc+ phenotype was maintained at a level of about 0.001%. When streaked on MSu plates, Suc+ NRRL Y-11430 gave raise to a mixture of fast and slow growing colonies. All attempts to purify the colonies of the fast growers were unsuccessful. The slow growing colonies were unequivocally demonstrated to represent Suc− segregants (progenies without plasmid) that originate from a population of Suc+ cells. These Suc− segregant cells cross-fed very efficiently on Suc+ cells. When allowed to grow for longer periods (3-4 days at 30° C.) they formed colonies as large as true Suc+ cells. This result provides evidence for the suggestion that a good portion of the invertase gene is secreted out of the Suc+ cells. The efficient cross-feeding under these growth conditions interfered with the ability to apply selection pressure for the maintenance of the SUC2 gene in NRRL Y-11430 cells.

Growth of Suc+ 11430 Under Limited Sucrose

In the studies described thus far, 1% sucrose was used to maintain the Suc+ phenotype. It was thought that a stronger selection pressure would be provided by propagating cells on low sucrose medium (0.05% sucrose). Unfortunately, even on 0.05% sucrose plates, the cross-feeding was prevalent.

After four days of growth in a shake flask on 0.05% sucrose, the stability of the Suc+ marker was around 2-4% compared to a value of 0.1% on richer sucrose medium (1% sucrose). See Table V for a summary of results.

Analysis of DNA from those cells retaining Suc+ phenotype by Southern hybridization indicated that the bulk of the SUC2 had integrated. Only a small amount of the plasmid was present in the autonomous state.

EXAMPLE III

An experiment was performed to see if it was possible to introduce pTSU1 into the HIS4 locus of the Pichia genome. Since pTSU1 has two SalI sites, which would generate two fragments upon completion digestion, a plasmid having one unique SalI site, located within the HIS4 gene locus and therefore only capable of generating one fragment upon complete digestion with SalI was prepared as follows.

Plasmid pTSU1 was digested to completion with NaeI, which freed three small NaeI fragments and left intact the major portion of the plasmid pTSU1. One of the two SalI sites originally contained within plasmid pTSU1 was lost along with the three small NaeI fragments which were excised by this procedure. Upon re-ligation of the NaeI-complete digest, pSR1, there was obtained a plasmid having the intact Pichia HIS4, PARS1 and the S. cerevisiae invertase gene, but only having one SalI site, located within the Pichia HIS4 gene.

pSR1 was then linearized with SalI and the linear fragment was isolated from a gel to eliminate contamination by small amounts of uncut pSR1 that may be present. The linear pSR1 was used to transform Pichia NRRL Y-11430. The regenerated cells were pooled and spread on MSu plates. Results are summarized in Table IV.

TABLE IV

Suc+ Colonies Obtained by Plating Aliquots of a
Pool of Regenerated Pichia NRRL 11430
Transformed with Linear Plasmid*

| Experiment | Number of Cells Plated | Number of Suc+ Colonies | Total/Suc+ |
|---|---|---|---|
| 11430 (pSR1-Linear) | $4 \times 10^7$ | 325 | $1.2 \times 10^5$ |
|  | $1.6 \times 10^8$ | 1600 | $1 \times 10^5$ |
|  | $3.2 \times 10^8$ | 2500 | $1.3 \times 10^5$ |
| 11430 (Control plasmid) | $2.5 \times 10^7$ | 0 | — |
|  | $1 \times 10^8$ | 0 | — |
|  | $2 \times 10^8$ | 0 | — |

*Pichia strain 11430 was transformed with linearized pSR1; the control plasmid used had no SUC2 gene. The transformed spheroplasts were regenerated on KDH (R) and at the end of three days post plating, the regenerated cells were pooled (see Example II, first paragraph) and aliquots plated on MSu to determine the number of Suc+ cells in the population. The total number of cells plated was determined by plating diluted aliquots on MD.

As expected, in the control experiment in which Pichia was transformed with an unrelated vector which did not contain the SUC2 gene, no Suc+ colonies were obtained. Sixteen Suc+ colonies were restreaked on MSu plates, of which ten gave a colony pattern suggestive of stable Suc+ phenotype, whereas the other 6 gave a mixture of fast and slow cross-feeding colonies. Thus, about 60% of the Suc+ transformants obtained using linearized pSR1 are presumably stable integrants.

DNA isolated from three of the stable transformants (Suc+ 10-1, Suc+ 11-1, and Suc+ 12-1) and one of the unstable transformants (Suc+ 9-1) were analyzed by Southern hybridization. In all the three stable transformants, the Southern hybridization pattern is in accordance with the pattern predicted for stable integration of the plasmid DNA. The Southern pattern obtained with the DNA from the unstable transformant Suc+ 9-1 indicates that the plasmid pSR1 is present solely in the autonomous (unintegrated) state. It is clear, from these results that SUC2 gene is a useful marker for introducing heterologous genes into the Pichia chromosome in a single step.

EXAMPLE IV

Growth Conditions for Chemostat Runs

Each chemostat run was performed using a Phillips designed two liter continuous fermentor equipped with monitors and controls for pH, dissolved oxygen (DO), agitator speed, temperature and airflow. Feed addition was achieved with a Milton-Roy Minipump. Feed was sterilized by autoclaving and maintained by filtration (Pall Ultipor Disposable Filter Assembly DFA 4001AR, 0.2 micron absolute). Each run was maintained at pH 4.0 by addition of $NH_3$ gas into the air stream. Temperature was held at 30° C. The dissolved oxygen concentration ranged from 45% to 80% air saturation. Chemostat working volume ranged from 1.3 to 2.1 liters. Cell density, productivity, and yields were determined from washed cell dry weights.

Each chemostat run was made under steady-state conditions where the dilution rate (D) was equal to the growth rate of the culture. Thus, the growth rate was controlled by adjusting the flow of fresh medium into the fermentor. Typical values for D ranged from 0.143 $hr^{-1}$ to 0.067 $hr^{-1}$.

Chemostat cultures were started with 5% inocula freshly grown in 100 ml of MM medium and sparged with 600 ml/min of filtered air. After depletion of the initial carbon source in the start-up medium, 1× FM-21 supplemented with 10% of the appropriate carbon source was pumped through the chemostat with a D value of 0.1 $hr^{-1}$. A 70% dissolved oxygen concentration was maintained by increasing airflow and supplementing with pure $O_2$ as required. A constant pH of 4.0 was maintained with periodic additions of $NH_3$. When the culture reached steady state and a cell density of about 50 g/l, the feed was switched to 2× FM-21 supplemented with 20% carbon source and allowed to reach steady state and a cell density of about 100 g/l. Finally, the feed was switched to 3× FM-21 supplemented with 30% carbon source and allowed to reach steady state. Then the feed pump rate and, therefore, the culture growth rate was increased to a D value of approximately 0.14 hr$^{-1}$ (corresponding to a generation time of about seven hours) and measurements of cell density, production rate and yield were made. Sucrose and glucose concentrations in the chemostat output were measured using Diastix glucose oxidase reagent strips (Miles Laboratories, Inc.).

Analyses of Suc+ Pichia Samples from High Cell Density Sucrose-chemostat

Cells obtained after growth of Suc+-Pichia strains in a sucrose chemostat to high cell density were analyzed to determine, (i) what fraction of cells retained the Suc+ phenotype and, (ii) the status of SUC2 gene (i.e., whether autonomous or chromosomally integrated). In the case of the chemostat samples of the NRRL Y-11430/Suc+ 3-14 construct, it was found that the frequency of Suc+ cells increased from an initial value of 1 per 30,000 to a value of 1 per 1,500 at the end of two cycles of growth in the chemostat. See Table V below.

TABLE V

| Stability of NRRL Y-11430/Suc+ Phenotype* | | | |
|---|---|---|---|
| Sample Source | Suc+ Total Cells | % Suc+ | Status of pTSU1 |
| First Sucrose Chemostat: | | | |
| 24h | 1/25,000 | 0.004 | ND** |
| 48h | 1/11,000 | 0.009 | Integrated |
| 120h (final sample) | 1/6000 | 0.017 | Integrated |
| Second Sucrose Chemostat: | | | |
| Final Sample | 1/1500 | 0.07 | Integrated |
| 72 h in Shake Flask on: | | | |
| MSu (1% Sucrose) | 1/1000 | 0.1 | ND |
| MD (1% Dextrose) | 1/100,000 | 0.001 | ND |
| Low MSu | | | Integrated |
| (0.05% Sucrose) | 1/50 | 2 | +Autonomous |

*11430/Suc+ 3-14 transformants grown under different conditions, were diluted, and aliquots plated on MSu to determine the percent of cells retaining the Suc+ phenotype. The total number of cells plated was determined by plating dilutions on MD plates. An aliquot of the final sample from the first chemostat cycle served as the inoculum for the second chemostat cycle. In shake flask experiments, similar results were obtained with all the three other Suc+ 11430-SC5 transformants (data not shown). Only on representative transformant (Suc+ 3-14) was tested in the chemostat.
**ND: Not determined.

Southern hybridization analysis was also carried out on these samples, which analysis indicated that the SUC2 gene was also present in association with chromosomal DNA. Because this construct performed well in the chemostat, we presently believe that a small percent (~0.07%) of Suc+ cells in the population will cause sufficient extracellular breakdown of sucrose to permit other cells to grow optimally. Under these conditions of growth, it may not be possible to enrich for Suc+ cells any further.

The examples have been provided merely to illustrate the practice of our invention and should not be read so as to limit the scope of our invention or the appended claims in any way. Reasonable variations and modifications, not departing from the essence and spirit of our invention, are contemplated to be within the scope of patent protection desired and sought.

We claim:

1. The pure culture comprising *Pichia pastoris* NRRL y-11430/pTSUI.

2. The pure culture comprising *Pichia pastoris* y-11430/pSR11.

3. The pure culture comprising *Pichia pastoris* NRRL y-15851/pSR1.

* * * * *